(12) United States Patent
Brueggemann et al.

(10) Patent No.: US 9,546,123 B2
(45) Date of Patent: Jan. 17, 2017

(54) PROCESS FOR PREPARING ACRYLIC ACID FROM FORMALDEHYDE AND ACETIC ACID

(71) Applicant: BASF SE, Ludwigshafen am Rhein (DE)

(72) Inventors: Till Christian Brueggemann, Ludwigshafen (DE); Nicolai Tonio Woerz, Darmstadt (DE); Astrid Ruppel, Ludwigshafen (DE)

(73) Assignee: BASF SE, Ludwigshafen am Rhein (DE)

( * ) Notice: Subject to any disclaimer, the term of this patent is extended or adjusted under 35 U.S.C. 154(b) by 0 days.

(21) Appl. No.: 14/972,255

(22) Filed: Dec. 17, 2015

(65) Prior Publication Data

US 2016/0176797 A1    Jun. 23, 2016

Related U.S. Application Data

(60) Provisional application No. 62/093,461, filed on Dec. 18, 2014.

(30) Foreign Application Priority Data

Dec. 18, 2014  (DE) ........................ 10 2014 019 081

(51) Int. Cl.
| | | |
|---|---|---|
| C07C 51/00 | (2006.01) | |
| B01J 8/00 | (2006.01) | |
| C07C 51/353 | (2006.01) | |
| B01J 23/22 | (2006.01) | |
| B01J 27/186 | (2006.01) | |
| C07C 57/04 | (2006.01) | |
| B01J 8/02 | (2006.01) | |

(52) U.S. Cl.
CPC ............ *C07C 51/353* (2013.01); *B01J 8/0278* (2013.01); *B01J 23/22* (2013.01); *B01J 27/186* (2013.01); *C07C 51/00* (2013.01); *C07C 57/04* (2013.01); *B01J 2208/00893* (2013.01); *B01J 2208/02* (2013.01)

(58) Field of Classification Search
CPC .................................. C07C 51/353; B01J 8/00
USPC ........................................... 562/599; 422/187
See application file for complete search history.

(56) References Cited

U.S. PATENT DOCUMENTS

2014/0343319 A1    11/2014 Goebel et al.

OTHER PUBLICATIONS

James F. Vitcha, et al., "Vapor Phase Aldol Reaction Acrylic Acid by the Reaction of Acetic Acid and Formaldehyde" I & EC Product Research and Development, vol. 5, No. 1, Mar. 1966, pp. 50-53.
International Search Report and Written Opinion issued Apr. 6, 2016 in PCT/EP2015/080193 (with English translation of categories of cited documents).

*Primary Examiner* — Sikarl Witherspoon
(74) *Attorney, Agent, or Firm* — Oblon, McClelland, Maier & Neustadt, L.L.P.

(57) ABSTRACT

The present invention relates to a process for preparing acrylic acid from formaldehyde and acetic acid, comprising reacting formaldehyde and acetic acid via an aldol condensation in a reaction unit comprising n reaction zones arranged in series, each comprising an aldol condensation catalyst, where n is at least 2, and wherein at least one stream leaving a reaction zone, before being fed into the reaction zone immediately downstream, is mixed with a stream comprising formaldehyde and optionally comprising acetic acid. The present invention further relates to an apparatus for preparing acrylic acid from formaldehyde and acetic acid and to the use of this apparatus.

24 Claims, 2 Drawing Sheets

PROCESS FOR PREPARING ACRYLIC ACID FROM FORMALDEHYDE AND ACETIC ACID

The present invention relates to a process for preparing acrylic acid from formaldehyde and acetic acid, comprising reacting formaldehyde and acetic acid via an aldol condensation in a reaction unit comprising n reaction zones arranged in series, each comprising an aldol condensation catalyst, where n is at least 2, to obtain a stream comprising acrylic acid, and wherein at least one stream leaving a reaction zone, before being fed into the reaction zone immediately downstream, is mixed with a stream comprising formaldehyde and optionally comprising acetic acid. The present invention further relates to an apparatus for preparing acrylic acid from formaldehyde and acetic acid and to the use of this apparatus.

The preparation of acrylic acid from formaldehyde and acetic acid in an aldol condensation with the aid of an aldol condensation catalyst generally gives significant amounts of unwanted by-products, combined with an unsatisfactory selectivity in terms of acrylic acid formation and the associated yield of acrylic acid.

Vitcha and Sims, I & EC Product Research and Development, Vol. 5, No. 1, March 1966, pages 50 to 53, state that, in the synthesis of acrylic acid in a gas phase reaction proceeding from acetic acid and formaldehyde at a molar ratio of 8:1 to 10:1, high conversions and yields of acrylic acid were observed. While this excess of acetic acid leads to a higher yield of acrylic acid, this results simultaneously in an incomplete acetic acid conversion which, in order to be able to operate such a preparation process in an economically viable manner, entails an appropriate workup of the product stream and associated apparatus complexity.

One problem underlying the invention was therefore that of providing an improved process for preparing acrylic acid from formaldehyde and acetic acid, especially with regard to selectivity in terms of acrylic acid formation and the associated yield of acrylic acid.

It has been found that, surprisingly, such a process can be provided by conducting the preparation of acrylic acid from formaldehyde and acetic acid in n reaction zones arranged in series, and feeding at least one reactant not completely to the first reaction zone but partly between two immediately successive reaction zones arranged in series.

The present invention therefore relates to a process for preparing acrylic acid from formaldehyde and acetic acid, comprising (a) providing a stream $S(0)$ comprising formaldehyde and acetic acid;
(b) reacting formaldehyde present in $S(0)$ with acetic acid present in $S(0)$ by means of an aldol condensation in a reaction unit comprising n reaction zones $R(x)$ arranged in series, each comprising an aldol condensation catalyst, where n is at least 2, to obtain a stream $S(n)$ comprising acrylic acid from the last reaction zone $R(n)$ of the reaction unit comprising the n reaction zones arranged in series, wherein the process comprises, for each reaction zone $R(x)$ of the reaction unit comprising the n reaction zones arranged in series:
(i) feeding a stream $S(x-1)$ into the reaction zone $R(x)$;
(ii) contacting the stream $S(x-1)$ with the aldol condensation catalyst present in the reaction zone $R(x)$ to obtain a stream $S(x)$ comprising acrylic acid;
(iii) removing the stream $S(x)$ from the reaction zone $R(x)$;

where, when x is less than n, the stream $S(x)$ additionally comprises acetic acid and, downstream of at least one of the reaction zones $R(x)$, the stream leaving this reaction zone $R(x)$ as stream $S(x)$, before being fed into the reaction zone $R(x+1)$ immediately downstream, is mixed with a stream $Z(x)$ comprising formaldehyde and optionally comprising acetic acid.

The process of the invention enables, in the case of an equimolar ratio of acetic acid and formaldehyde assessed over all the reactant streams used or an only slight molar excess of acetic acid based on formaldehyde, generation of a local excess of acetic acid over formaldehyde, combined with a higher selectivity in terms of acrylic acid formation and the associated yield of acrylic acid.

Providing a Stream $S(0)$ in (a)

In step (a) of the present process, a stream $S(0)$ comprising formaldehyde and acetic acid is provided.

In principle, stream $S(0)$ is not restricted in terms of the molar ratio of formaldehyde and acetic acid. Preferably, the molar ratio of acetic acid to formaldehyde in stream $S(0)$ is in the range from 2:1 to 15:1, preferably from 2:1 to 10:1, further preferably from 2:1 to 5:1.

Useful sources for the acetic acid in principle include any suitable source comprising at least a proportion of acetic acid. This may be acetic acid fed fresh to the process. It may likewise be acetic acid which has not been converted in the above-described process and which, for example after removal from the product stream in one or more workup steps, is recycled into the process. A combination of acetic acid fed fresh to the process and acetic acid recycled into the process is likewise possible.

Useful sources for the formaldehyde likewise in principle include any suitable source comprising at least a proportion of formaldehyde. This may be formaldehyde fed fresh to the process. It may likewise be formaldehyde which has not been converted in the above-described process and which, for example after removal from the product stream in one or more workup steps, is recycled into the process. A combination of formaldehyde fed fresh to the process and formaldehyde recycled into the process is likewise possible. For example, the source used for the formaldehyde may be an aqueous formaldehyde solution (formalin). It is likewise possible to use a formaldehyde source which affords formaldehyde, for instance trioxane or paraformaldehyde. Preferably, the source used for the formaldehyde is an aqueous formaldehyde solution. Preferably, the aqueous formaldehyde solution has a formaldehyde content in the range from 20% to 85% by weight, preferably from 30% to 80% by weight, further preferably from 40% to 60% by weight.

In principle, stream $S(0)$ is also unrestricted in terms of further components present. Thus, it is possible that stream $S(0)$ comprises at least one further component as well as acetic acid and formaldehyde. The at least one further component may, for example, be water, nitrogen, oxygen, methanol, acrylic acid or a mixture of at least two thereof. Preferably, stream $S(0)$ therefore comprises at least one further component selected from the group consisting of water, nitrogen, oxygen and a mixture of at least two thereof. Further preferably, stream $S(0)$ comprises, as at least one further component, water or nitrogen or water and nitrogen, further preferably water and nitrogen.

Useful sources for the nitrogen likewise in principle include any suitable source comprising at least a proportion of nitrogen. For example, it is possible to use pure nitrogen or, when oxygen is present in addition to nitrogen, air, for example ambient air or synthetic air. Preference is thus given to using, when nitrogen and oxygen are present, air as the nitrogen and oxygen source.

In principle, the stream S(0) which preferably comprises water and nitrogen as well as formaldehyde and acetic acid is not restricted in terms of its content of these four components. Preferably, stream S(0) consists of formaldehyde, acetic acid, water and nitrogen to an extent of at least 95% by volume, preferably to an extent of 95% to 99% by volume, further preferably to an extent of 96% to 98% by volume.

In principle, stream S(0) is also unrestricted in terms of its nitrogen content. Preferably, stream S(0) comprises up to 90% by volume of nitrogen, the nitrogen content of stream S(0) preferably being in the range from 10% to 90% by volume, further preferably from 15% to 85% by volume.

Therefore, stream S(0) preferably consists to an extent of at least 95% by volume of formaldehyde, acetic acid, water and nitrogen, the nitrogen content of stream S(0) comprising up to 90% by volume. Further preferably, stream S(0) preferably consists to an extent of 96% to 98% by volume of formaldehyde, acetic acid, water and nitrogen, the nitrogen content of stream S(0) being in the range from 40% to 85% by volume.

In principle, stream S(0) is unrestricted in terms of its acetic acid content. Preferably, the acetic acid content of stream S(0) is in the range from 5% to 60% by volume, preferably from 7% to 50% by volume.

In principle, stream S(0) is unrestricted in terms of its formaldehyde content. Preferably, the formaldehyde content of stream S(0) is in the range from 1% to 25% by volume, further preferably 2% to 20% by volume.

In principle, stream S(0) is unrestricted in terms of its water content. Preferably, the water content of stream S(0) is in the range from 1% to 30% by volume, further preferably from 3% to 25% by volume.

Preferably, the acetic acid content of stream S(0) is in the range from 5% to 60% by volume, the formaldehyde content in the range from 1% to 25% by volume and the water content in the range from 1% to 30% by volume, the acetic acid content further preferably being in the range from 7% to 50% by volume, the formaldehyde content in the range from 2% to 20% by volume and the water content in the range from 3% to 25% by volume.

Stream S(0) can be provided by the contacting of at least one stream comprising acetic acid with at least one stream comprising formaldehyde. Equally, stream S(0) can be provided by the contacting of at least one stream comprising acetic acid with at least one stream comprising formaldehyde and optionally water. Equally, stream S(0) can be provided by the contacting of at least one stream comprising acetic acid with at least one stream comprising nitrogen and at least one stream comprising formaldehyde and optionally water.

Equally, stream S(0) can be provided by the contacting of at least one stream comprising acetic acid with at least one stream comprising nitrogen and the contacting of the resulting stream comprising acetic acid and nitrogen with at least one stream comprising formaldehyde and optionally water. Equally, stream S(0) can be provided by the contacting of at least one stream comprising acetic acid with at least one stream comprising formaldehyde and optionally water and the contacting of the resulting stream comprising acetic acid and formaldehyde and optionally water with at least one stream comprising nitrogen. Equally, stream S(0) can be provided by the contacting of at least one stream comprising formaldehyde and optionally water with at least one stream comprising nitrogen and the contacting of the resulting stream comprising formaldehyde and optionally water and nitrogen with at least one stream comprising acetic acid.

Preferably, stream S(0) is provided by the contacting of a stream comprising acetic acid with a stream comprising nitrogen and a stream comprising formaldehyde and water.

Stream S(0) can in principle be fed to the first reaction zone R(1) in liquid or gaseous form or partly in liquid form and partly in gaseous form. Preferably, stream S(0) is fed to the first reaction zone R(1) in gaseous form.

With regard to the stream S(0) fed to the first reaction zone R(1) preferably in gaseous form, it is possible in the present case that the components of the stream present in liquid form or dissolved in a liquid under standard conditions are vaporized together or separately from one another.

Stream S(0) can in principle be fed to the first reaction zone R(1) at any suitable temperature. Preferably, stream S(0) is fed to the first reaction zone R(1) at a temperature at which it is entirely in gaseous form. Further preferably, stream S(0) is fed to the first reaction zone R(1) at a temperature in the range from 150 to 450° C., preferably from 200 to 400° C., further preferably from 250 to 390° C.

Reacting Formaldehyde with Acetic Acid in (b)

In step (b) of the present process, formaldehyde present in S(0) is reacted with acetic acid present in S(0) by means of an aldol condensation in a reaction unit comprising n reaction zones R(x) arranged in series, each comprising an aldol condensation catalyst, where n is at least 2, to obtain a stream S(n) comprising acrylic acid from the last reaction zone R(n) of the reaction unit comprising the n reaction zones arranged in series, wherein the process comprises, for each reaction zone R(x) of the reaction unit comprising the n reaction zones arranged in series:
  (i) feeding a stream S(x−1) into the reaction zone R(x);
  (ii) contacting the stream S(x−1) with the aldol condensation catalyst present in the reaction zone R(x) to obtain a stream S(x) comprising acrylic acid;
  (iii) removing the stream S(x) from the reaction zone R(x);
where, when x is less than n, the stream S(x) additionally comprises acetic acid and, downstream of at least one of the reaction zones R(x), the stream leaving this reaction zone R(x) as stream S(x), before being fed into the reaction zone R(x+1) immediately downstream, is mixed with a stream Z(x) comprising formaldehyde and optionally comprising acetic acid.

Reaction Unit Comprising n Reaction Zones R(x) Arranged in Series

The reaction unit in (b) comprises n reaction zones R(x) arranged in series, each comprising an aldol condensation catalyst, where n is at least 2.

Provided that the reaction unit comprises at least 2 reaction zones R(x), there is no further restriction in the reaction unit in terms of the number of reaction zones R(x). The number n may therefore assume, for example, the values of 2, 3, 4, 5, 6, 7, 8, 9, 10, 11 or 12. Preferably in the context of the present invention, n is a number in the range from 2 to 10, where n is further preferably 2, 3, 4 or 5.

The at least 2 reaction zones R(x) may be disposed in one reactor or else in a plurality of different reactors. If n is 2, the two reaction zones may thus be disposed in one reactor or else in separate reactors. If n is 3, the first two reaction zones may be disposed in a first reactor and the third reaction zone in a second reactor, or the first reaction zone in a first reactor and the last two reaction zones in a second reactor, or the first reaction zone in a first reactor, the second reaction zone in a second reactor and the third reaction zone in a third reactor. Preferably, the reaction zones are reaction zones of a single reactor.

Therefore, it is preferable that n is 2, 3, 4 or 5, and the reaction zones R(1) and R(2) and optionally R(3), R(4) and R(5) are reaction zones of a single reactor.

The reaction zones R(x) may be the same or different in terms of the catalyst volume present therein. For example, it is possible that all the reaction zones R(x) have the same catalyst volume or that two reaction zones have the same catalyst volume and this catalyst volume is greater or less than a third reaction zone or the further reaction zones.

In principle, it is possible to use any reactor or any combination of reactors which allows continuous performance of the present process. Thus, examples of useful reactors include tubular reactors, especially shell and tube reactors, either operated isothermally or in the form of an adiabatic shell and tube reactor with internal heat exchange, fixed bed reactors, fluidized bed reactors, moving bed reactors, salt bath reactors and staged reactors. In the present case, the regions which each comprise aldol condensation catalyst and are arranged in parallel in a shell and tube reactor or staged reactor with respect to the stream flowing through the reactor are understood to be one reaction zone R(x).

If at least one staged reactor is used, it is preferable in the present case that the individual stages are configured adiabatically and the staged reactor is optionally configured with intermediate cooling between at least two stages, preferably between all the stages. The intermediate cooling can be effected by all the present suitable methods or combinations thereof known to those skilled in the art. Thus, it is conceivable in the context of the present process that the intermediate cooling of a stream S(x) before feeding to the reaction zone immediately downstream is effected with the aid of a fluid, for example with the aid of a heat exchanger, in which case the fluid prior to the heat exchange has a lower temperature than the stream S(x) leaving the respective reaction zone R(x). It is likewise conceivable that a stream Z(x) to be fed in is fed in at a temperature which leads to lowering of the temperature of the respective stream S(x). It is likewise conceivable that the intermediate cooling is effected by a combination of the two methods mentioned.

The reactors may be arranged vertically or horizontally. If at least one reactor is arranged vertically, it is possible that it is operated with an upward or downward flow.

When n is 2, preference is given to using a shell and tube reactor. When n is 3, preference is likewise given to using a shell and tube reactor or a staged reactor. When n is 4 or 5, preference is given to using a staged reactor.

The reaction zones R(x) each comprising an aldol condensation catalyst are preferably fixed bed reaction zones in which the reactants flow around the aldol condensation catalyst. Further preferably, each reaction zone R(x) of the reaction unit comprising n reaction zones R(x) arranged in series is a fixed bed reaction zone in a shell and tube reactor or a staged reactor.

Therefore, it is preferable that n is 2 or 3, the reaction zones R(1) and R(2) and optionally R(3) are reaction zones of a single reactor, and each reaction zone R(x) of the reaction unit comprising n reaction zones R(x) arranged in series is a fixed bed reaction zone in a shell and tube reactor, or that n is 3, 4 or 5, the reaction zones R(1), R(2), R(3) and optionally R(4) and R(5) are reaction zones of a single reactor, and each reaction zone R(x) of the reaction unit comprising n reaction zones R(x) arranged in series is a fixed bed reaction zone in a staged reactor.

In the context of the present application, it is conceivable that the process is conducted in two, three or more, preferably two or three, preferably in three, reaction units which are arranged in series and comprise n reaction zones R(x) arranged in series, these reaction units preferably being operated in A/B mode, such that, for example, only one reaction unit or two reaction units are operated simultaneously. Preferably, therefore, the process is conducted in two, three or more, preferably two or three, preferably in three, reaction units which are arranged in series and comprise n reaction zones R(x) arranged in series, these reaction units being operated in A/B mode.

Aldol Condensation Catalyst

The term "aldol condensation catalyst" in the present context is understood to mean any catalyst capable of catalyzing an aldol condensation of the two compounds formaldehyde and acetic acid to give acrylic acid.

In principle, all suitable aldol condensation catalysts are useful in accordance with the invention. Examples, used as unsupported catalysts or in supported form, are alkali metal or alkaline earth metal oxides, mixed oxides comprising vanadium oxide, aluminosilicates or zeolites. Preferably, the aldol condensation catalyst comprises vanadium and optionally phosphorus and optionally oxygen, further preferably vanadium, phosphorus and oxygen, further preferably a vanadium-phosphorus oxide. Further preferably, the aldol condensation catalyst comprises a vanadium-phosphorus oxide having the general empirical formula $V_2O_x(PO_4)_y$, where x is preferably in the range from 1.0 to 2.75, further preferably from 1.5 to 2.25, and y is preferably in the range from 1.5 to 2.5, further preferably from 1.8 to 2.3.

The aldol condensation catalyst may take the form of an unsupported catalyst or may be in supported form on at least one support material. If the aldol condensation catalyst is present in supported form on at least one support material, the at least one support material is preferably selected from the group consisting of $SiO_2$, $TiO_2$, $Al_2O_3$ and $ZrO_2$, mixed oxides of two or more thereof and mixtures of two or more thereof. Preferably, the aldol condensation catalyst is used in the form of an unsupported catalyst.

The aldol condensation catalyst may be present, for example, as granules or extrudates in the form of cylinders, spheres, hollow cylinders, in star form, in tablet form or as a mixture thereof. Preferably, the aldol condensation catalyst is in the form of extrudates, the cross section of the extrudates having a rectangular, triangular, hexagonal, square, polygonal, oval or circular shape. Particular preference is given to using an aldol condensation catalyst in extrudates with a round cross section, the diameter of the round cross-sectional area being in the range from 0.1 to 100 mm, preferably in the range from 0.2 to 80 mm, further preferably in the range from 0.5 to 50 mm, further preferably in the range from 1 to 30 mm, and the length of the extrudates being in the range from 0.1 to 100 mm, preferably in the range from 0.5 to 80 mm, further preferably in the range from 1 to 70 mm.

In principle, different aldol condensation catalysts may be used in different reaction zones R(x). It is likewise possible that the same aldol condensation catalyst is used in at least two reaction zones R(x). Further preferably, the same aldol condensation catalyst is used in all reaction zones R(x).

Process Parameters in (b)

In principle, the present process can be conducted at all temperatures at which a stream S(n) comprising acrylic acid is obtained in (b). Thus, it is possible that the temperature in the different reaction zones R(x) has different values. It is likewise possible that the temperature in the different reaction zones R(x) has the same value. Preferably, the reacting in (b) is effected in at least one reaction zone R(x), preferably in all reaction zones R(x), at a temperature in the range from 300 to 400° C., preferably from 310 to 390° C., further preferably from 320 to 370° C. This temperature is understood to mean the temperature of the respective stream S(x−1) immediately before it comes into contact with the aldol condensation catalyst, measured with a thermocouple (NiCrNi).

In principle, the present process can be conducted at all pressures at which a stream S(n) comprising acrylic acid is obtained in (b). Thus, it is possible that the pressure in the different reaction zones R(x) has different values. It is likewise possible that the pressure in the different reaction zones R(x) has the same value. Preferably, the reacting in (b) is effected at a pressure in the range from 1 to 5 bar, preferably in the range from 1 to 2 bar. All pressures in the present context should be understood as absolute values.

Preferably, the reacting in (b) is therefore effected at a temperature in the range from 300 to 400° C. and a pressure in the range from 1 to 5 bar, further preferably at a temperature in the range from 320 to 370° C. and a pressure in the range from 1 to 2 bar.

The space velocity (weight hourly space velocity, WHSV) with respect to the reacting in (b) is preferably chosen such that an advantageous balance of conversion, selectivity, yield, reactor geometry, reactor dimensions and process regime is obtained. In the context of present invention, space velocity is understood to mean the sum total of the mass of all the streams fed to the catalyst mass in all reaction zones and time. Preferably, the WHSV is in the range from 1 to 5 kg/kg/h, further preferably in the range from 1.2 to 3 kg/kg/h.

Preferably, the reacting in (b) is therefore effected at a temperature in the range from 300 to 400° C., a pressure in the range from 1 to 5 bar and a WHSV of 1 to 5 kg/kg/h, further preferably at a temperature in the range from 320 to 370° C., a pressure in the range from 1 to 2 bar and a WHSV in the range from 1.2 to 3 kg/kg/h.

Stream Z(x)

The present process comprises, for each reaction zone R(x) of the n reaction zones arranged in series,
 (i) feeding a stream S(x−1) into the reaction zone R(x);
 (ii) contacting the stream S(x−1) with the aldol condensation catalyst present in the reaction zone R(x) to obtain a stream S(x) comprising acrylic acid;
 (iii) removing the stream S(x) from the reaction zone R(x);
where, when x is less than n, the stream S(x) additionally comprises acetic acid and, downstream of at least one of the reaction zones R(x), the stream leaving this reaction zone R(x) as stream S(x), before being fed into the reaction zone R(x+1) immediately downstream, is mixed with a stream Z(x) comprising formaldehyde and optionally comprising acetic acid.

Therefore, downstream of at least one of the reaction zones R(x) where x is less than n, the stream leaving this reaction zone R(x) is mixed with a stream Z(x) before being fed to the reaction zone R(x+1) immediately downstream. When n is 2, the stream S(1) leaving the reaction zone R(1) is thus mixed with a stream Z(x). When n is 3, the stream S(1) leaving the reaction zone R(1) is mixed with a stream Z(1) or the stream S(2) leaving the reaction zone R(2) is mixed with a stream Z(2), or the stream S(1) leaving the reaction zone R(1) is mixed with a stream Z(1) and the stream S(2) leaving the reaction zone R(2) is mixed with a stream Z(2).

Preferably, one stream Z(x) in each case is fed in between all the successive reaction zones R(x) and R(x+1).

If more than one stream Z(x) is fed in, it is possible that these streams differ in terms of the components present and in terms of the proportions of the components present. It is likewise possible that at least two of these streams are identical in terms of composition. The components and proportions described hereinafter with regard to a stream Z(x) should thus be understood as being descriptive of all the streams Z(x) fed in in the present process, although the streams Z(x) should in principle be regarded independently in terms of the components present and the corresponding proportions. Preferably, all the streams Z(x) fed in are identical in terms of composition.

At least one stream Z(x), preferably all the streams Z(x), comprising formaldehyde and optionally acetic acid is/are not restricted in terms of further components present. Thus, it is possible that at least one further component is present, selected from the group consisting of water, oxygen, nitrogen, methanol and a mixture of two or more thereof.

Stream Z(x), preferably all streams Z(x), comprising formaldehyde and optionally acetic acid and oxygen comprise preferably from 0.1% to 20% by volume, preferably from 5% to 10% by volume, of oxygen.

Stream Z(x), preferably all streams Z(x), consist(s) of water and formaldehyde preferably to an extent of 80% by volume or more, preferably to an extent of 90% by volume or more, preferably to an extent of 95% by volume or more, further preferably to an extent of 98% by volume or more, where the weight ratio of water and formaldehyde is not restricted in principle. Preferably, the weight ratio of water and formaldehyde here is in the range from 2:1 to 1:2, further preferably from 1.1:1 to 1:1.1. Preferably, therefore, the stream Z(x), preferably all streams Z(x), consist(s) of water and formaldehyde to an extent of 80% by volume or more, preferably to an extent 90% by volume or more, preferably to an extent of 95% by volume or more, further preferably to an extent of 98% by volume or more, where the weight ratio of water and formaldehyde is in the range from 2:1 to 1:2, preferably from 1.1:1 to 1:1.1.

A stream Z(x) may be provided in any manner suitable in the present context. Thus, it is possible that, if n is greater than 2 and more than 1 stream is provided, the streams Z(x) are each provided separately. It is likewise possible that a single stream is suitably divided and then fed to the process in the form of separate streams Z(x). It is additionally possible that a stream comprising formaldehyde and optionally water, which is used to provide the stream S(0), before being mixed with a stream comprising acetic acid, is suitably divided, so as to obtain at least one stream Z(x) to be fed to the process.

Preferably, the providing in (a) of the present process therefore comprises
 (a-1) providing a stream comprising formaldehyde and water;
 (a-2) dividing this stream comprising formaldehyde and water into at least one stream Z(x) for feeding to the process and a further stream comprising formaldehyde and water;
 (a-3) mixing the further stream with a stream comprising acetic acid and optionally a stream comprising nitrogen to obtain stream S(0).

The molar ratio of the total amount of acetic acid fed in via streams S(0) and optionally Z(x) to the total amount of formaldehyde fed in via streams S(0) and Z(x) is not restricted in principle, provided that a stream S(n) comprising acrylic acid is obtained from the last reaction zone R(n) of the reaction unit comprising the n reaction zones arranged in series.

Preferably, the molar ratio of the total amount of acetic acid fed in via streams S(0) and optionally Z(x) to the total amount of formaldehyde fed in via streams S(0) and Z(x) is equal to or greater than 1:1. It is thus possible that the molar ratio is chosen such that the two components are used in equimolar amounts.

It is likewise possible that the molar ratio is chosen such that an excess of acetic acid is used. Further preferably, the molar ratio of the total amount of acetic acid fed in via streams S(0) and optionally Z(x) to the total amount of formaldehyde fed in via streams S(0) and Z(x) is therefore in the range from 1:1 to 3:1, further preferably from 1:1 to 2:1, further preferably from 1:1 to 1.5:1. More preferably, the molar ratio of the total amount of acetic acid fed in via streams S(0) and optionally Z(x) to the total molar amount of formaldehyde fed in via streams S(0) and Z(x) is 1:1.

As described, the process of the invention enables, in the case of an equimolar ratio of acetic acid and formaldehyde assessed over all the reactant streams used or an only slight molar excess of acetic acid based on formaldehyde, through the feeding-in of a stream Z(x) or a plurality of streams Z(x), generation of a local excess of acetic acid over formaldehyde, combined with a higher selectivity in terms of acrylic acid formation and the associated yield of acrylic acid.

In a preferred embodiment, n is 2, in which case the providing in (a) comprises
(a-1) providing a stream comprising formaldehyde and water;
(a-2) dividing, preferably halving, the stream of (a-1) into a stream Z(1) for feeding to the process and a further stream comprising formaldehyde and water;
(a-3) mixing the further stream with a stream comprising acetic acid and optionally a stream comprising nitrogen to obtain stream S(0).

Preferably, in this embodiment, reaction zones R(1) and R(2) are fixed bed reaction zones, for which any suitable reactor or combination of reactors is an option in principle. Further preferably, in this embodiment, reaction zones R(1) and R(2) are fixed bed reaction zones in a shell and tube reactor and optionally have the same catalyst volume.

Preferably, therefore, in this embodiment, n is 2, in which case the providing in (a) comprises
(a-1) providing a stream comprising formaldehyde and water;
(a-2) dividing, preferably halving, the stream of (a-1) into a stream Z(1) for feeding to the process and a further stream comprising formaldehyde and water;
(a-3) mixing the further stream with a stream comprising acetic acid and optionally a stream comprising nitrogen to obtain stream S(0),
where reaction zones R(1) and R(2) are fixed bed reaction zones in a shell and tube reactor and optionally have the same catalyst volume.

In principle, stream S(0) in this embodiment is not restricted in terms of the proportions of the components present therein. Preferably, in this embodiment, the content in stream S(0) of acetic acid is in the range from 9% to 45% by volume, that of formaldehyde in the range from 3% to 20% by volume and that of water in the range from 5% to 30% by volume, the content of acetic acid further preferably being in the range from 10% to 35% by volume, that of formaldehyde in the range from 5% to 18% by volume and that of water in the range from 8% to 28% by volume.

Preferably, therefore, in this embodiment, n is 2, in which case the providing in (a) comprises
(a-1) providing a stream comprising formaldehyde and water;
(a-2) dividing, preferably halving, the stream of (a-1) into a stream Z(1) for feeding to the process and a further stream comprising formaldehyde and water;
(a-3) mixing the further stream with a stream comprising acetic acid and optionally a stream comprising nitrogen to obtain stream S(0),
where reaction zones R(1) and R(2) are fixed bed reaction zones in a shell and tube reactor and optionally have the same catalyst volume, and
where the content in stream S(0) of acetic acid is in the range from 9% to 45% by volume, that of formaldehyde in the range from 3% to 20% by volume and that of water in the range from 5% to 30% by volume, the content of acetic acid preferably being in the range from 10% to 35% by volume, that of formaldehyde in the range from 5% to 18% by volume and that of water in the range from 8% to 28% by volume.

Further preferably, in this embodiment, the molar ratio of the total amount of acetic acid fed in via streams S(0) and optionally Z(x) to the total amount of formaldehyde fed in via streams S(0) and Z(x) is equal to or greater than 1:1, preferably in the range from 1:1 to 3:1, further preferably in the range from 1:1 to 2:1, further preferably in the range from 1:1 to 1.5:1 and further preferably 1:1.

Preferably, stream Z(1) in this embodiment consists of water and formaldehyde to an extent of 98% by volume or more, where the weight ratio of water and formaldehyde is in the range from 1.1:1 to 1:1.1.

Therefore, the present invention also relates to a process comprising
(a) providing a stream S(0) comprising formaldehyde and acetic acid;
(b) reacting formaldehyde present in S(0) with acetic acid present in S(0) by means of an aldol condensation in a reaction unit comprising n reaction zones R(x) arranged in series, each comprising an aldol condensation catalyst, where n is at least 2, to obtain a stream S(n) comprising acrylic acid from the last reaction zone R(n) of the reaction unit comprising the n reaction zones arranged in series, wherein the process comprises, for each reaction zone R(x) of the reaction unit comprising the n reaction zones arranged in series:
(i) feeding a stream S(x−1) into the reaction zone R(x);
(ii) contacting the stream S(x−1) with the aldol condensation catalyst present in the reaction zone R(x) to obtain a stream S(x) comprising acrylic acid;
(iii) removing the stream S(x) from the reaction zone R(x);
where, when x is less than n, the stream S(x) additionally comprises acetic acid and, downstream of at least one of the reaction zones R(x), the stream leaving this reaction zone R(x) as stream S(x), before being fed into the reaction zone R(x+1) immediately downstream, is mixed with a stream Z(x) comprising formaldehyde and optionally comprising acetic acid, where n is 2 and where the providing in (a) comprises
(a-1) providing a stream comprising formaldehyde and water;
(a-2) dividing, preferably halving, the stream of (a-1) into a stream Z(1) for feeding to the process and a further stream comprising formaldehyde and water;

(a-3) mixing the further stream with a stream comprising acetic acid and optionally a stream comprising nitrogen to obtain stream S(0);

where reaction zones R(1) and R(2) are fixed bed reaction zones in a shell and tube reactor and optionally have the same catalyst volume, and where the content in stream S(0) of acetic acid is in the range from 9% to 45% by volume, that of formaldehyde in the range from 3% to 20% by volume and that of water in the range from 5% to 30% by volume, the content of acetic acid preferably being in the range from 10% to 35% by volume, that of formaldehyde in the range from 5% to 18% by volume and that of water in the range from 8% to 28% by volume, where the molar ratio of the total amount of acetic acid fed in via streams S(0) and optionally Z(x) to the total molar amount of formaldehyde fed in via streams S(0) and Z(x) is in the range from 1:1 to 2:1, and where stream Z(1) consists of water and formaldehyde to an extent of 98% by volume or more, where the weight ratio of water and formaldehyde is in the range from 1.1:1 to 1:1.1.

In a further preferred embodiment, n is 3, in which case the providing in (a) comprises
(a-1) providing a stream comprising formaldehyde and water;
(a-2) dividing, preferably into thirds, the stream of (a-1) into two streams Z(1) and Z(2) for feeding to the process and a further stream comprising formaldehyde and water;
(a-3) mixing the further stream with a stream comprising acetic acid and optionally a stream comprising nitrogen to obtain stream S(0).

Preferably, in this embodiment, reaction zones R(1), R(2) and R(3) are fixed bed reaction zones, for which any suitable reactor or combination of reactors is an option in principle. Further preferably, in this embodiment, reaction zones R(1), R(2) and R(3) are fixed bed reaction zones in a shell and tube reactor or a staged reactor and optionally have the same catalyst volume.

Preferably, therefore, in this embodiment, n is 3, in which case the providing in (a) comprises
(a-1) providing a stream comprising formaldehyde and water;
(a-2) dividing, preferably into thirds, the stream of (a-1) into two streams Z(1) and Z(2) for feeding to the process and at least one further stream comprising formaldehyde and water;
(a-3) mixing the further stream with a stream comprising acetic acid and optionally a stream comprising nitrogen to obtain stream S(0), where reaction zones R(1), R(2) and R(3) are fixed bed reaction zones in a shell and tube reactor or a staged reactor and optionally have the same catalyst volume.

In principle, stream S(0) in this embodiment is not restricted in terms of the proportions of the components present therein. Preferably, in this embodiment, the content in stream S(0) of acetic acid is in the range from 9% to 50% by volume, that of formaldehyde in the range from 3% to 20% by volume and that of water in the range from 5% to 30% by volume, the content of acetic acid preferably being in the range from 10% to 45% by volume, that of formaldehyde in the range from 3% to 15% by volume and that of water in the range from 5% to 25% by volume.

Preferably, therefore, in this embodiment, n is 3, in which case the providing in (a) comprises
(a-1) providing a stream comprising formaldehyde and water;
(a-2) dividing, preferably into thirds, the stream of (a-1) into two streams Z(1) and Z(2) for feeding to the process and at least one further stream comprising formaldehyde and water;
(a-3) mixing the further stream with a stream comprising acetic acid and optionally a stream comprising nitrogen to obtain stream S(0), where reaction zones R(1), R(2) and R(3) are fixed bed reaction zones in a shell and tube reactor or a staged reactor and optionally have the same catalyst volume, and where the content in stream S(0) of acetic acid is in the range from 9% to 50% by volume, that of formaldehyde in the range from 3% to 20% by volume and that of water in the range from 5% to 30% by volume, the content of acetic acid preferably being in the range from 10% to 45% by volume, that of formaldehyde in the range from 3% to 15% by volume and that of water in the range from 5% to 25% by volume.

Further preferably, in this embodiment, the molar ratio of the total amount of acetic acid fed in via streams S(0) and optionally Z(x) to the total amount of formaldehyde fed in via streams S(0) and Z(x) is equal to or greater than 1:1, preferably in the range from 1:1 to 3:1, further preferably in the range from 1:1 to 2:1, further preferably in the range from 1:1 to 1.5:1 and further preferably 1:1.

Preferably, streams Z(1) and Z(2) in this embodiment consist of water and formaldehyde to an extent of 98% by volume or more, where the weight ratio of water and formaldehyde is in the range from 1.1:1 to 1:1.1.

Therefore, the present invention also relates to a process comprising:
(a) providing a stream S(0) comprising formaldehyde and acetic acid;
(b) reacting formaldehyde present in S(0) with acetic acid present in S(0) by means of an aldol condensation in a reaction unit comprising n reaction zones R(x) arranged in series, each comprising an aldol condensation catalyst, where n is at least 2, to obtain a stream S(n) comprising acrylic acid from the last reaction zone R(n) of the reaction unit comprising the n reaction zones arranged in series, wherein the process comprises, for each reaction zone R(x) of the reaction unit comprising the n reaction zones arranged in series:
(i) feeding a stream S(x−1) into the reaction zone R(x);
(ii) contacting the stream S(x−1) with the aldol condensation catalyst present in the reaction zone R(x) to obtain a stream S(x) comprising acrylic acid;
(iii) removing the stream S(x) from the reaction zone R(x);

where, when x is less than n, the stream S(x) additionally comprises acetic acid and, downstream of at least one of the reaction zones R(x), the stream leaving this reaction zone R(x) as stream S(x), before being fed into the reaction zone R(x+1) immediately downstream, is mixed with a stream Z(x) comprising formaldehyde and optionally comprising acetic acid,
where n is 3 and where the providing in (a) comprises
(a-1) providing a stream comprising formaldehyde and water;
(a-2) dividing, preferably into thirds, the stream of (a-1) into two streams Z(1) and Z(2) for feeding to the process and a further stream comprising formaldehyde and water;

(a-3) mixing the further stream with a stream comprising acetic acid and optionally a stream comprising nitrogen to obtain stream S(0), where reaction zones R(1), R(2) and R(3) are fixed bed reaction zones in a shell and tube reactor or a staged reactor and optionally have the same catalyst volume, and where the content in stream S(0) of acetic acid is in the range from 9% to 50% by volume, that of formaldehyde in the range from 3% to 20% by volume and that of water in the range from 5% to 30% by volume, the content of acetic acid preferably being in the range from 10% to 45% by volume, that of formaldehyde in the range from 3% to 15% by volume and that of water in the range from 5% to 25% by volume, where the molar ratio of the total amount of acetic acid fed in via streams S(0) and optionally Z(x) to the total amount of formaldehyde fed in via streams S(0) and Z(x) is in the range from 1:1 to 2:1, and where streams Z(1) and Z(2) consist of water and formaldehyde to an extent of 98% by volume or more, where the weight ratio of water and formaldehyde is in the range from 1.1:1 to 1:1.1.

In a further preferred embodiment, n is 4, in which case the reaction zones R(1), R(2), R(3) and R(4) are fixed bed reaction zones in a staged reactor.

In this embodiment, therefore, n is 4, in which case the providing in (a) comprises (a-1) providing a stream comprising formaldehyde and water;

(a-2) dividing, preferably into quarters, the stream of (a-1) into three streams Z(1), Z(2) and Z(3) for feeding to the process and a further stream comprising formaldehyde and water;

(a-3) mixing the further stream with a stream comprising acetic acid and optionally a stream comprising nitrogen to obtain stream S(0), and where reaction zones R(1), R(2), R(3) and R(4) are fixed bed reaction zones in a staged reactor and optionally have the same catalyst volume.

In principle, stream S(0) in this embodiment is not restricted in terms of the proportions of the components present therein. Preferably, in this embodiment, the content in stream S(0) of acetic acid is in the range from 9% to 55% by volume, that of formaldehyde in the range from 2% to 20% by volume and that of water in the range from 4% to 30% by volume, the content of acetic acid preferably being in the range from 10% to 50% by volume, that of formaldehyde in the range from 2% to 15% by volume and that of water in the range from 4% to 25% by volume.

Preferably, therefore, in this embodiment, n is 4, in which case the providing in (a) comprises (a-1) providing a stream comprising formaldehyde and water;

(a-2) dividing, preferably into quarters, the stream of (a-1) into three streams Z(1), Z(2) and Z(3) for feeding to the process and a further stream comprising formaldehyde and water;

(a-3) mixing the further stream with a stream comprising acetic acid and optionally a stream comprising nitrogen to obtain stream S(0), and where reaction zones R(1), R(2), R(3) and R(4) are fixed bed reaction zones in a staged reactor and optionally have the same catalyst volume, and where the content in stream S(0) of acetic acid is in the range from 9% to 55% by volume, that of formaldehyde in the range from 2% to 20% by volume and that of water in the range from 4% to 30% by volume, the content of acetic acid preferably being in the range from 10% to 50% by volume, that of formaldehyde in the range from 2% to 15% by volume and that of water in the range from 4% to 25% by volume.

Further preferably, in this embodiment, the molar ratio of the total amount of acetic acid fed in via streams S(0) and optionally Z(x) to the total amount of formaldehyde fed in via streams S(0) and Z(x) is equal to or greater than 1:1, preferably in the range from 1:1 to 3:1, further preferably in the range from 1:1 to 2:1, further preferably in the range from 1:1 to 1.5:1 and further preferably 1:1.

Preferably, streams Z(1), Z(2) and Z(3) in this embodiment consist of water and formaldehyde to an extent of 98% by volume or more, where the weight ratio of water and formaldehyde is in the range from 1.1:1 to 1:1.1.

Therefore, the present invention also relates to a process comprising:

(a) providing a stream S(0) comprising formaldehyde and acetic acid;

(b) reacting formaldehyde present in S(0) with acetic acid present in S(0) by means of an aldol condensation in a reaction unit comprising n reaction zones R(x) arranged in series, each comprising an aldol condensation catalyst, where n is at least 2, to obtain a stream S(n) comprising acrylic acid from the last reaction zone R(n) of the reaction unit comprising the n reaction zones arranged in series, wherein the process comprises, for each reaction zone R(x) of the reaction unit comprising the n reaction zones arranged in series:

(i) feeding a stream S(x−1) into the reaction zone R(x);

(ii) contacting the stream S(x−1) with the aldol condensation catalyst present in the reaction zone R(x) to obtain a stream S(x) comprising acrylic acid;

(iii) removing the stream S(x) from the reaction zone R(x);

where, when x is less than n, the stream S(x) additionally comprises acetic acid and, downstream of at least one of the reaction zones R(x), the stream leaving this reaction zone R(x) as stream S(x), before being fed into the reaction zone R(x+1) immediately downstream, is mixed with a stream Z(x) comprising formaldehyde and optionally comprising acetic acid, where n is 4 and where the providing in (a) comprises (a-1) providing a stream comprising formaldehyde and water;

(a-2) dividing, preferably into quarters, the stream of (a-1) into three streams Z(1), Z(2) and Z(3) for feeding to the process and a further stream comprising formaldehyde and water;

(a-3) mixing the further stream with a stream comprising acetic acid and optionally a stream comprising nitrogen to obtain stream S(0), and where reaction zones R(1), R(2), R(3) and R(4) are fixed bed reaction zones in a staged reactor and optionally have the same catalyst volume, and where the content in stream S(0) of acetic acid is in the range from 9% to 55% by volume, that of formaldehyde in the range from 2% to 20% by volume and that of water in the range from 4% to 30% by volume, the content of acetic acid preferably being in the range from 10% to 50% by volume, that of formaldehyde in the range from 2% to 15% by volume and that of water in the range from 4% to 25% by volume, where the molar ratio of the total amount of acetic acid fed in via streams S(0) and optionally Z(x) to the total amount of formaldehyde fed in via streams S(0) and Z(x) is in the range from 1:1 to 2:1, and where streams Z(1), Z(2) and Z(3) consist of water and formaldehyde to an extent of 98% by volume or more, where the weight ratio of water and formaldehyde is in the range from 1.1:1 to 1:1.1.

In a further preferred embodiment, n is 5, in which case the reaction zones R(1), R(2), R(3), R(4) and R(5) are fixed bed reaction zones in a staged reactor.

In this embodiment, therefore, n is 5, in which case the providing in (a) comprises
- (a-1) providing a stream comprising formaldehyde and water;
- (a-2) dividing, preferably into fifths, the stream of (a-1) into four streams Z(1), Z(2), Z(3) and Z(4) for feeding to the process and a further stream comprising formaldehyde and water;
- (a-3) mixing the further stream with a stream comprising acetic acid and optionally a stream comprising nitrogen to obtain stream S(0), where reaction zones R(1), R(2), R(3), R(4) and R(5) are fixed bed reaction zones in a staged reactor and optionally have the same catalyst volume.

In principle, stream S(0) in this embodiment is not restricted in terms of the proportions of the components present therein. Preferably, in this embodiment, the content in stream S(0) of acetic acid is in the range from 9% to 60% by volume, that of formaldehyde in the range from 2% to 20% by volume and that of water in the range from 3% to 30% by volume, the content of acetic acid preferably being in the range from 10% to 55% by volume, that of formaldehyde in the range from 2% to 15% by volume and that of water in the range from 3% to 20% by volume.

Preferably, therefore, in this embodiment, n is 5, in which case the providing in (a) comprises
- (a-1) providing a stream comprising formaldehyde and water;
- (a-2) dividing, preferably into fifths, the stream of (a-1) into four streams Z(1), Z(2), Z(3) and Z(4) for feeding to the process and a further stream comprising formaldehyde and water;
- (a-3) mixing the further stream with a stream comprising acetic acid and optionally a stream comprising nitrogen to obtain stream S(0), where reaction zones R(1), R(2), R(3), R(4) and R(5) are fixed bed reaction zones in a staged reactor and optionally have the same catalyst volume, and where the content in stream S(0) of acetic acid is in the range from 9% to 60% by volume, that of formaldehyde in the range from 2% to 20% by volume and that of water in the range from 3% to 30% by volume, the content of acetic acid preferably being in the range from 10% to 55% by volume, that of formaldehyde in the range from 2% to 15% by volume and that of water in the range from 3% to 20% by volume.

Further preferably, in this embodiment, the molar ratio of the total amount of acetic acid fed in via streams S(0) and optionally Z(x) to the total amount of formaldehyde fed in via streams S(0) and Z(x) is equal to or greater than 1:1, preferably in the range from 1:1 to 3:1, further preferably in the range from 1:1 to 2:1, further preferably in the range from 1:1 to 1.5:1 and further preferably 1:1.

Preferably, streams Z(1), Z(2), Z(3) and Z(4) in this embodiment consist of water and formaldehyde to an extent of 98% by volume or more, where the weight ratio of water and formaldehyde is in the range from 1.1:1 to 1:1.1.

Therefore, the present invention also relates to a process comprising:
- (a) providing a stream S(0) comprising formaldehyde and acetic acid;
- (b) reacting formaldehyde present in S(0) with acetic acid present in S(0) by means of an aldol condensation in a reaction unit comprising n reaction zones R(x) arranged in series, each comprising an aldol condensation catalyst, where n is at least 2, to obtain a stream S(n) comprising acrylic acid from the last reaction zone R(n) of the reaction unit comprising the n reaction zones arranged in series, wherein the process comprises, for each reaction zone R(x) of the reaction unit comprising the n reaction zones arranged in series:
  - (i) feeding a stream S(x−1) into the reaction zone R(x);
  - (ii) contacting the stream S(x−1) with the aldol condensation catalyst present in the reaction zone R(x) to obtain a stream S(x) comprising acrylic acid;
  - (iii) removing the stream S(x) from the reaction zone R(x);

where, when x is less than n, the stream S(x) additionally comprises acetic acid and, downstream of at least one of the reaction zones R(x), the stream leaving this reaction zone R(x) as stream S(x), before being fed into the reaction zone R(x+1) immediately downstream, is mixed with a stream Z(x) comprising formaldehyde and optionally comprising acetic acid, where n is 5 and where the providing in (a) comprises
- (a-1) providing a stream comprising formaldehyde and water;
- (a-2) dividing, preferably into fifths, the stream of (a-1) into four streams Z(1), Z(2), Z(3) and Z(4) for feeding to the process and a further stream comprising formaldehyde and water;
- (a-3) mixing the further stream with a stream comprising acetic acid and optionally a stream comprising nitrogen to obtain stream S(0), where reaction zones R(1), R(2), R(3), R(4) and R(5) are fixed bed reaction zones in a staged reactor and optionally have the same catalyst volume, and where the content in stream S(0) of acetic acid is in the range from 9% to 60% by volume, that of formaldehyde in the range from 2% to 20% by volume and that of water in the range from 3% to 30% by volume, the content of acetic acid preferably being in the range from 10% to 55% by volume, that of formaldehyde in the range from 2% to 15% by volume and that of water in the range from 3% to 20% by volume, where the molar ratio of the total amount of acetic acid fed in via streams S(0) and optionally Z(x) to the total amount of formaldehyde fed in via streams S(0) and Z(x) is in the range from 1:1 to 2:1, and where streams Z(1), Z(2), Z(3) and Z(4) consist of water and formaldehyde to an extent of 98% by volume or more, where the weight ratio of water and formaldehyde is in the range from 1.1:1 to 1:1.1.

In a further embodiment of the present process, it is conceivable that stream Z(x) comprises acetic acid and optionally formaldehyde, and the molar ratio of the total amount of formaldehyde fed in via streams S(0) and Z(x) to the total amount of acetic acid fed in via streams S(0) and Z(x) is greater than 1:1, and preferably in the range from 1.1:1 to 3:1, further preferably from 1.1:1 to 2:1, further preferably from 1.1:1 to 1.5:1. In this case, the molar ratio of formaldehyde to acetic acid in stream S(0) is preferably in the range from 2:1 to 15:1, preferably in the range from 2:1 to 10:1, further preferably in the range from 2:1 to 5:1. In this case, stream Z(x) consists of acetic acid preferably to an extent of at least 30% by volume, further preferably to an extent of at least 40% by volume, further preferably to an extent of at least 50% by volume, further preferably to an extent of at least 70% by volume, further preferably to an extent of at least 90% by volume.

Further Steps

The process of the invention may comprise one or more further steps in addition to steps (a) and (b). Thus, the process of the invention may additionally comprise the regenerating of the aldol condensation catalyst of (b), for example by means of a thermal treatment. In principle, such a regeneration will be effected when either the conversion of one or more reactants or/and the selectivity based on acrylic acid goes below particular values defined within the process design. Moreover, such a regeneration can be effected either within the reactor used for the aldol condensation or outside this reactor, or partly within and partly outside the reactor.

Workup

The stream S(n) comprising acrylic acid obtained in (b) is not restricted in principle in terms of its further use. Thus, it is possible that the stream S(n) is fed to one or more workup operations. The one or more workup operations may serve to further increase the purity of the acrylic acid obtained. They may likewise serve to suitably remove one or more components present in stream S(n) and optionally to recycle them at least partly into the process, in order thus to obtain a highly integrated process.

For example, it is possible that stream S(n) is subjected to one or more thermal separations, for example one or more distillations, preferably one or more rectifications, in order, for example, to remove formaldehyde or water or formaldehyde and water, and to recycle them at least partly into the process, optionally after one or more further workup operations.

The stream S(n) obtained in (b) may in principle be at any suitable temperature. Preferably, the stream S(n) obtained in (b) is at a temperature in the range from 320 to 430° C., further preferably in the range from 330 to 420° C. The stream S(n) may in principle be used further at said temperature. In the process of the invention, it is preferable that the stream S(n) obtained in (b) is suitably cooled. The heat released in the course of this cooling can be utilized suitably in the process.

Thus, it is possible that the stream S(n) obtained in (b), either without prior cooling or after prior cooling as described above, is stored intermediately in one or more buffer vessels, preferably in one buffer vessel, before it is used further. One reason why intermediate storage is preferable is in order to balance out any possible slight variations in the composition of stream S(n) which may occur in the course of operation of the overall process, which is preferably continuous in accordance with the invention, and thus to ensure that a downstream process stage is supplied continuously with a stream having a comparatively more constant composition over time. According to the design of the overall process, it is preferable, for example, to intermediately store an amount of stream S(n) which occurs over a period in the range from 1 to 20 h, preferably from 3 to 15 h, further preferably from 4 to 12 h, in one or more than one, preferably one, buffer vessel. The one or more than one, preferably one, buffer vessel is generally kept at the feed temperature or a temperature below the feed temperature.

Preferably, the stream S(n) obtained in (b), optionally after cooling and/or intermediate storage in one or more buffer vessels, is fed to a further process stage (c), in order to remove, in an appropriate manner in application terms, any water present and/or any water and formaldehyde present alongside acrylic acid in stream S(n) from acrylic acid in this at least one process stage, which gives rise to a stream A2 enriched in acrylic acid compared to stream S(n). It is further preferable that, in this additional process stage, as well as stream A2, a stream A1 depleted of acrylic acid compared to stream S(n) is formed.

With regard to this removing in (c), this can be effected by any suitable method or combination of methods. Preferably, the removing is effected by rectification. For rectificative separation, it is possible in principle to use any suitable apparatus or any suitable combination of apparatuses. Preference is given here to using at least one column, further preferably one or two columns, further preferably one column, having separating internals in accordance with the invention. Particular preference is given to using one column operated as a rectification column with separating internals; further preference is given to using a column operated as a rectification column and having mass transfer trays as separating internals.

In principle, the acrylic acid-depleted stream A2 can be withdrawn in the stripping section of the column, in the rectifying section of the column or from the bottom of the column. Preferably, stream A2 is withdrawn from the bottom of the column.

Preferably, stream A2 is fed to at least one further process stage, it being preferable to obtain, in this at least one further process stage, a stream enriched once again with respect to acrylic acid compared to A2. Preferably, the stream A2 obtained in (c) is therefore fed to a further process stage (d).

With regard to the removing in (d), this can be effected by any suitable method or combination of methods. Preferably, the removing in (d) is effected by rectification. For rectificative separation, it is possible in principle to use any suitable apparatus or any suitable combination of apparatuses. Preference is given here to using at least one column, further preferably one or two columns, further preferably one column, having separating internals in accordance with the invention. Particular preference is given to using one column operated as a rectification column with separating internals; further preference is given to using a column operated as a rectification column and having mass transfer trays, preferably dual flow trays, as separating internals.

In (d), at least one stream A3 enriched in acrylic acid and/or acrylic acid adducts compared to A2 is obtained. This at least one stream may consist of one or more individual streams. In the context of the present invention, the at least one stream A3 preferably consists of at least two individual streams, further preferably at least the gaseous stream A3*a* and the liquid stream A3*b*. These two individual streams are preferably withdrawn from the stripping section or from the bottom of a column, preferably from the bottom of a column, preferably from the bottom of a rectification column.

The term "acrylic acid adducts" as used in the context refers to components formed reversibly, preferably components formed reversibly and having a higher standard boiling point of acrylic acid, which form through dimerization or oligomerization of acrylic acid.

In principle, stream A3*a* can be withdrawn in the stripping section of the column, in the rectifying section of the column or from the bottom of the column. Preferably, stream A3*a* is withdrawn as a side draw, preferably as a gaseous side draw, from the column, further preferably as a gaseous side draw in the stripping section of the column.

In principle, the stream A3*a* withdrawn from the column in (d) as a gaseous side draw in the stripping section of the column is not restricted in terms of its further use. For example, it is possible to commercially utilize stream A3*a* as a crude acrylic acid stream, to send it to a process other than that according to the invention or to upgrade it through one or more than one further process step to give a glacial acrylic acid stream. Useful upgrading methods include, for example, a rectificative fine purification, a crystallization or an azeotropic distillation using one or more than one suitable auxiliary.

The stream A3b withdrawn in liquid form from the bottom of the column in (d) can be fed to one or more than one further process step, in order to dissociate any dimers and/or oligomers of acrylic acid present to acrylic acid. For dissociation of any dimers and/or oligomers of acrylic acid present in stream A3b, it is possible in principle to use any suitable apparatus or any suitable combination of apparatuses. Preference is given here to using at least one column, further preferably one or two columns, further preferably one column, having separating internals in accordance with the invention. Particular preference is given to using one column operated as a rectification column with separating internals; further preference is given to using a column operated as a rectification column and having mass transfer trays, preferably dual flow trays, as separating internals.

Apparatus for Preparing Acrylic Acid from Formaldehyde and Acetic Acid

As well as the process described for preparing acrylic acid from formaldehyde and acetic acid, the present invention also relates to an apparatus for preparing acrylic acid from formaldehyde and acetic acid, comprising a reaction unit comprising
  (I) n reaction zones R(x) arranged in series, wherein the n reaction zones R(x) arranged in series each comprise an aldol condensation catalyst, preferably in fixed bed form; and
  (II) y feed devices for the feeding of at least one stream Z(x) comprising formaldehyde and optionally acetic acid, with one feed device in each case disposed between one reaction zone R(x) and one reaction zone R(x+1) directly downstream, and where y is an integer and is less than n.

Use of the Apparatus for Preparing Acrylic Acid from Formaldehyde and Acetic Acid As well as the process described for preparing acrylic acid from formaldehyde and acetic acid and the apparatus described for preparing acrylic acid from formaldehyde and acetic acid, the present invention also relates to the use of the apparatus described for preparing acrylic acid from formaldehyde and acetic acid.

The present invention is illustrated in detail by the following embodiments and combinations of embodiments which are apparent from the corresponding dependency references and other references:

1. A process for preparing acrylic acid from formaldehyde and acetic acid, comprising
   (a) providing a stream S(0) comprising formaldehyde and acetic acid;
   (b) reacting formaldehyde present in S(0) with acetic acid present in S(0) by means of an aldol condensation in a reaction unit comprising n reaction zones R(x) arranged in series, each comprising an aldol condensation catalyst, where n is at least 2, to obtain a stream S(n) comprising acrylic acid from the last reaction zone R(n) of the reaction unit comprising the n reaction zones arranged in series, wherein the process comprises, for each reaction zone R(x) of the reaction unit comprising the n reaction zones arranged in series:
      (i) feeding a stream S(x−1) into the reaction zone R(x);
      (ii) contacting the stream S(x−1) with the aldol condensation catalyst present in the reaction zone R(x) to obtain a stream S(x) comprising acrylic acid;
      (iii) removing the stream S(x) from the reaction zone R(x);
   where, when x is less than n, the stream S(x) additionally comprises acetic acid and, downstream of at least one of the reaction zones R(x), the stream leaving this reaction zone R(x) as stream S(x), before being fed into the reaction zone R(x+1) immediately downstream, is mixed with a stream Z(x) comprising formaldehyde and optionally comprising acetic acid.
2. The process according to embodiment 1, wherein n is a number in the range from 2 to 10, where n is preferably 2, 3, 4 or 5.
3. The process according to embodiment 1 or 2, wherein the reaction zones R(x) are reaction zones of a single reactor.
4. The process according to embodiment 3, wherein each of the reaction zones R(x) is a fixed bed reaction zone, preferably in a shell and tube reactor or a staged reactor.
5. The process according to any of embodiments 1 to 4, wherein the molar ratio of the total amount of acetic acid fed in via streams S(0) and optionally Z(x) to the total amount of formaldehyde fed in via streams S(0) and Z(x) is equal to or greater than 1:1, preferably in the range from 1:1 to 3:1, further preferably from 1:1 to 2:1, further preferably from 1:1 to 1.5:1 and further preferably 1:1.
6. The process according to any of embodiments 1 to 5, wherein the molar ratio of acetic acid to formaldehyde in stream S(0) is in the range from 2:1 to 15:1, preferably in the range from 2:1 to 10:1, further preferably in the range from 2:1 to 5:1.
7. The process according to any of embodiments 1 to 6, wherein stream S(0), as well as formaldehyde and acetic acid, comprises at least one further component, preferably selected from the group consisting of water, nitrogen, oxygen and a mixture of at least two thereof, wherein stream S(0) further preferably comprises water or nitrogen or water and nitrogen, further preferably water and nitrogen.
8. The process according to embodiment 7, wherein stream S(0) consists of formaldehyde, acetic acid, water and nitrogen to an extent of at least 95% by volume, preferably to an extent of 95% to 99% by volume, further preferably to an extent of 96% to 98% by volume.
9. The process according to embodiment 7 or 8, wherein stream S(0) comprises up to 90% by volume of nitrogen, the nitrogen content of stream S(0) preferably being in the range from 10% to 90% by volume, further preferably from 15% to 85% by volume.
10. The process according to any of embodiments 1 to 9, wherein at least one stream Z(x), in addition to formaldehyde and optionally acetic acid, comprises at least one further component selected from the group consisting of water, oxygen, nitrogen and a mixture thereof.
11. The process according to any of embodiments 1 to 10, wherein at least one stream Z(x), preferably all the streams Z(x), comprise(s) from 0.1% to 20% by volume, preferably from 5% to 10% by volume, of oxygen.
12. The process according to any of embodiments 1 to 11, wherein at least one stream Z(x), preferably all the streams Z(x), consist(s) of water and formaldehyde to an extent of 80% by volume or more, preferably to an extent of 90% by volume or more, preferably to an extent of 95% by volume or more, further preferably to an extent of 98% by volume or more, where the weight ratio of water and formaldehyde is preferably in the range from 2:1 to 1:2, preferably from 1.1:1 to 1:1.1.

13. The process according to any of embodiments 1 to 12, wherein all the streams Z(x) fed in are identical in terms of composition.

14. The process according to any of embodiments 1 to 13, wherein one stream Z(x) in each case is fed in between all the successive reaction zones R(x) and R(x+1).

15. The process according to any of embodiments 1 to 14, wherein the aldol condensation catalyst in at least one reaction zone R(x), preferably in all the reaction zones R(x), comprises vanadium and optionally phosphorus and optionally oxygen, preferably vanadium, phosphorus and oxygen, further preferably a vanadium-phosphorus oxide, preferably having the general empirical formula $V_2O_x$ $(PO_4)_y$, where x is preferably in the range from 1.0 to 2.75, further preferably from 1.5 to 2.25, and y is preferably in the range from 1.5 to 2.5, further preferably from 1.8 to 2.3.

16. The process according to any of embodiments 1 to 15, wherein the providing in (a) comprises:
    (a-1) providing a stream comprising formaldehyde and water;
    (a-2) dividing this stream comprising formaldehyde and water into at least one stream Z(x) for feeding to the process and a further stream comprising formaldehyde and water;
    (a-3) mixing the further stream with a stream comprising acetic acid and optionally a stream comprising nitrogen to obtain stream S(0).

17. The process according to any of embodiments 1 to 16, wherein n is 2 and wherein the providing in (a) comprises:
    (a-1) providing a stream comprising formaldehyde and water;
    (a-2) dividing, preferably halving, the stream of (a-1) into a stream Z(1) for feeding to the process and a further stream comprising formaldehyde and water;
    (a-3) mixing the further stream with a stream comprising acetic acid and optionally a stream comprising nitrogen to obtain stream S(0).

18. The process according to embodiment 17, wherein reaction zones R(1) and R(2) are fixed bed reaction zones, preferably in a shell and tube reactor, and optionally have the same catalyst volume.

19. The process according to embodiment 17 or 18, wherein the content in stream S(0) of acetic acid is in the range from 9% to 45% by volume, that of formaldehyde in the range from 3% to 20% by volume and that of water in the range from 5% to 30% by volume, the content of acetic acid preferably being in the range from 10% to 35% by volume, that of formaldehyde in the range from 5% to 18% by volume and that of water in the range from 8% to 28% by volume.

20. The process according to any of embodiments 1 to 16, wherein n is 3 and wherein the providing in (a) comprises:
    (a-1) providing a stream comprising formaldehyde and water;
    (a-2) dividing, preferably into thirds, the stream of (a-1) into two streams Z(1) and Z(2) for feeding to the process and a further stream comprising formaldehyde and water;
    (a-3) mixing the further stream with a stream comprising acetic acid and optionally a stream comprising nitrogen to obtain stream S(0).

21. The process according to embodiment 20, wherein reaction zones R(1), R(2) and R(3) are fixed bed reaction zones, preferably in a shell and tube reactor or staged reactor, and optionally have the same catalyst volume.

22. The process according to embodiment 20 or 21, wherein the content in stream S(0) of acetic acid is in the range from 9% to 50% by volume, that of formaldehyde in the range from 3% to 20% by volume and that of water in the range from 5% to 30% by volume, the content of acetic acid preferably being in the range from 10% to 45% by volume, that of formaldehyde in the range from 3% to 15% by volume and that of water in the range from 5% to 25% by volume.

23. The process according to any of embodiments 1 to 16, wherein n is 4 and wherein the providing in (a) comprises:
    (a-1) providing a stream comprising formaldehyde and water;
    (a-2) dividing, preferably into quarters, the stream of (a-1) into three streams Z(1), Z(2) and Z(3) for feeding to the process and a further stream comprising formaldehyde and water;
    (a-3) mixing the further stream with a stream comprising acetic acid and optionally a stream comprising nitrogen to obtain stream S(0).

24. The process according to embodiment 23, wherein reaction zones R(1), R(2), R(3) and R(4) are fixed bed reaction zones, preferably in a staged reactor, and optionally have the same catalyst volume.

25. The process according to either of embodiments 23 and 24, wherein the content in stream S(0) of acetic acid is in the range from 9% to 55% by volume, that of formaldehyde in the range from 2% to 20% by volume and that of water in the range from 4% to 30% by volume, the content of acetic acid preferably being in the range from 10% to 50% by volume, that of formaldehyde in the range from 2% to 15% by volume and that of water in the range from 4% to 25% by volume.

26. The process according to any of embodiments 1 to 16, wherein n is 5 and wherein the providing in (a) comprises:
    (a-1) providing a stream comprising formaldehyde and water;
    (a-2) dividing, preferably into fifths, the stream of (a-1) into four streams Z(1), Z(2), Z(3) and Z(4) for feeding to the process and a further stream comprising formaldehyde and water;
    (a-3) mixing the further stream with a stream comprising acetic acid and optionally a stream comprising nitrogen to obtain stream S(0).

27. The process according to embodiment 26, wherein reaction zones R(1), R(2), R(3), R(4) and R(5) are fixed bed reaction zones, preferably in a staged reactor, and optionally have the same catalyst volume.

28. The process according to embodiment 26 or 27, wherein the content in stream S(0) of acetic acid is in the range from 9% to 60% by volume, that of formaldehyde in the range from 2% to 20% by volume and that of water in the range from 3% to 30% by volume, the content of acetic acid preferably being in the range from 10% to 55% by volume, that of formaldehyde in the range from 2% to 15% by volume and that of water in the range from 3% to 20% by volume.

29. The process according to any of embodiments 1 to 28, wherein the reacting in (b) is effected in at least one reaction zone R(x), preferably in all reaction zones R(x), at a temperature in the range from 300 to 400° C., preferably from 310 to 390° C., further preferably from 320 to 370° C.

30. The process according to any of embodiments 1 to 29, wherein the reacting in (b) is effected in at least one reaction zone R(x), preferably in all reaction zones R(x), at a pressure in the range from 1 to 5 bar, preferably in the range from 1 to 2 bar.
31. The process according to any of embodiments 1 to 30, wherein the space velocity (WHSV), defined as the ratio of the sum total of the mass of all the streams fed in to the catalyst mass in all reaction zones and time, is in the range from 1 to 5 kg/kg/h, preferably in the range from 1.2 to 3 kg/kg/h.
32. An apparatus for preparing acrylic acid from formaldehyde and acetic acid, comprising a reaction unit comprising
   (I) n reaction zones R(x) arranged in series, wherein the n reaction zones R(x) arranged in series each comprise an aldol condensation catalyst, preferably in fixed bed form; and
   (II) y feed devices for the feeding of at least one stream Z(x) comprising formaldehyde and optionally acetic acid, with one feed device in each case disposed between one reaction zone R(x) and one reaction zone R(x+1) directly downstream, and where y is an integer and is less than n.
33. The use of an apparatus according to embodiment 32 for preparation of acrylic acid from formaldehyde and acetic acid, comprising
   (a) providing a stream S(0) comprising formaldehyde and acetic acid;
   (b) reacting formaldehyde present in S(0) with acetic acid present in S(0) by means of an aldol condensation in a reaction unit comprising n reaction zones R(x) arranged in series, each comprising an aldol condensation catalyst, where n is at least 2, to obtain a stream S(n) comprising acrylic acid from the last reaction zone R(n) of the reaction unit comprising the n reaction zones arranged in series, wherein the process comprises, for each reaction zone R(x) of the reaction unit comprising the n reaction zones arranged in series:
      (i) feeding a stream S(x−1) into the reaction zone R(x);
      (ii) contacting the stream S(x−1) with the aldol condensation catalyst present in the reaction zone R(x) to obtain a stream S(x) comprising acrylic acid;
      (iii) removing the stream S(x) from the reaction zone R(x);
   where, when x is less than n, the stream S(x) additionally comprises acetic acid and, downstream of at least one of the reaction zones R(x), the stream leaving this reaction zone R(x) as stream S(x), before being fed into the reaction zone R(x+1) immediately downstream, is mixed with a stream Z(x) comprising formaldehyde and optionally comprising acetic acid.

The present invention is illustrated in detail by the examples which follow.

EXAMPLES

I. Gas Chromatography

For gas chromatography, an instrument of the Agilent 7890 type with an FFAP column was used. The temperature program was as follows:
hold at 40° C. for 10 min;
heat to 90° C. at a heating rate of 2 K/min;
heat to 200° C. at a heating rate of 6 K/min;
heat to 250° C. at a heating rate of 25 K/min;
hold at 250° C. for 10 min.

II. Setup and Operation of the Pilot Plant

Comparative Example without Side Feed (V1)

The apparatus consisted of a fixed bed reactor (bed length about 90 cm, diameter 16 mm, 1.4541 stainless steel) heated in four zones and having 3 sampling points for online GC measurements (inlet, middle, outlet) and two reactant metering zones. In order to charge the plant with formaldehyde and acetic acid, the reservoir vessel was initially charged with acetic acid or acetic acid solution and formaldehyde or formalin solution.

Formalin (49% by weight of formaldehyde in water) was conveyed by means of a Fink HPLC pump and evaporated completely by means of a microevaporator (passage length 60 mm, passage width 0.2 mm, alloy 22, 2.4602) (wall temperature about 280° C.). In order to prevent paraformaldehyde from precipitating out in the cold pipe, the reservoir vessel and the distance up to the evaporator were heated to 60° C. By means of a three-way tap, it was possible to run formalin either in a circuit back into the vessel or else in the evaporator direction.

A Fink HPLC pump was used to pump acetic acid into a helical tube evaporator (diameter 8 mm, length about 2 m, 1.4571 stainless steel), which completely evaporated therein (wall temperature about 200° C.) and mixed with a stream comprising nitrogen.

Figure 1:
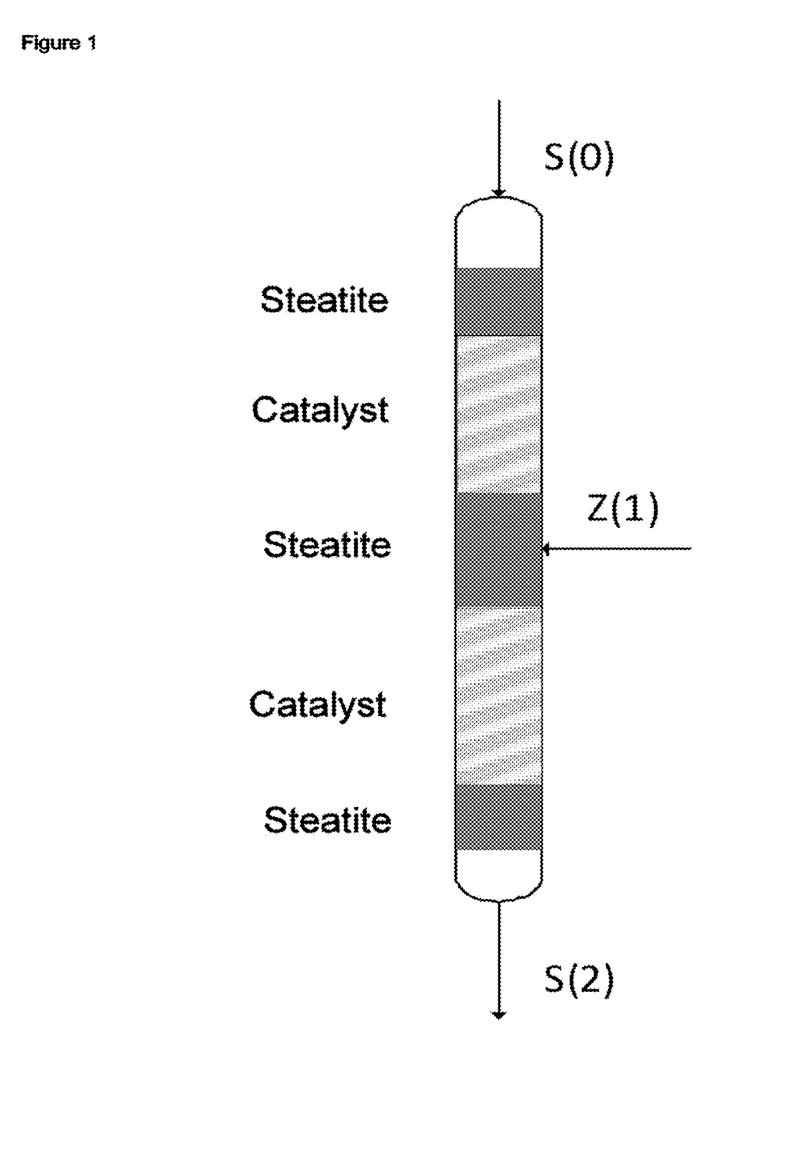
FIG. 1 shows a schematic of the experimental setup in example 1 having a reaction unit comprising 2 reaction zones R(1) and R(2) arranged in series, each comprising an aldol condensation catalyst, and streams S(0), S(1) and Z(1).

The stream comprising the evaporated formalin and the stream comprising the evaporated acetic acid and nitrogen were combined and passed via a pipeline heated to 150-200° C. through a static mixer (diameter 10 mm, length 80 mm, 1.4541 stainless steel) containing wire mesh into the reactor heated to 320° C. (WHSV: 1.4 kg/kg/h). The filling profile of the reactor is shown in FIG. 1. After passing through an unfilled region (length 2.8 cm), the gas stream arrived at a first steatite bed (mass 33 g, bed height 16 cm, 4-5 mm balls). The downstream catalyst bed was divided into two (mass of each 40 g, bed height 23 cm) and was interspersed with a second steatite bed (mass 42 g, bed height 20 cm, 4-5 mm balls). In the middle of this second steatite bed was the optional side feed. The overall bed rested on a catalyst support of about 3 cm in height, with a third steatite bed (mass 14 g, bed height 7 cm, 4-5 mm balls) concluding the reactor outlet. Within the reactor was a thermowell of thickness 3.17 mm, which was used to measure a temperature profile along the reactor. The catalyst used comprised vanadium and phosphorus.

The reactor offgas was passed to a total combustion unit downstream of the reactor outlet. For protection against blockages by catalyst dusts, a filter station was installed downstream of the reactor outlet. In the total combustion unit, all components were incinerated with air metered in additionally (about 2000 L (STP)/h) and nitrogen which can be metered in additionally (about 1000 L (STP)/h) to give water and carbon dioxide. Constant pressure conditions in the reactor over different test runs were established by partly throttling the valves in the filter station. The total combustion unit air was heated to 300-400° C. by means of heating sleeves. The combustion temperature in the combustion catalyst bed varied with the organic carbon loading of the reactor offgases and was between 250° C. and 500° C. The offgas from the total combustion unit was passed through a separator (T=5-15° C.). The offgas that remains thereafter was passed into the offgas conduit.

Inventive Example with Side Feeding (V2)

The experimental setup and operation of the plant were analogous to the above description. Two alterations should be mentioned:

The reservoir vessel for the acetic acid was initially charged with a mixture of acetic acid and formalin, which were evaporated S(0) in the helical tube evaporator.

The evaporated formalin stream from the microevaporator was not passed upstream of the static mixer at the reactor inlet as described above, but metered in the middle of the catalyst bed (Z(1)).

The table below gives an overview of the total flow rates of S(0) and Z(1) metered in. The reactor temperature (outer wall) was 320° C. in both cases and the reaction was conducted at a pressure of 1100 mbar.

TABLE 1

Reactor feeds for comparative example V1 and inventive example V2

| | Feed S(0) | | | | | Feed Z(1) | | | | |
|---|---|---|---|---|---|---|---|---|---|---|
| | $N_2$ [L (STP)/h] | AA [g/h] | FA [g/h] | MeOH [g/h] | $H_2O$ [g/h] | $N_2$ [L (STP)/h] | AA [g/h] | FA [g/h] | MeOH [g/h] | $H_2O$ [g/h] |
| V1 | 20 | 68.0 | 17.2 | 0.7 | 17.2 | 0.0 | 0.0 | 0.0 | 0.0 | 0.0 |
| V2 | 20 | 68.0 | 8.5 | 0.3 | 8.5 | 0.0 | 0.0 | 8.7 | 0.4 | 8.7 |

AA: acetic acid
FA: formaldehyde
MeOH: methanol
L (STP): standard liters

The reactant stream S(0) and the product stream S(2) were analyzed by gas chromatography. The carbon-based acrylic acid selectivity based on the total carbon measured at the outlet is plotted against the carbon conversion in FIG. 2.

(1) The carbon conversion (C) is calculated as follows:

$$C = 100 * ((NC^P_{total} - NC^P_{ACE} - NC^P_{FA})/NC^P_{total})$$

with
$NC^P_{total}$ = number of carbon atoms present in the product stream S(2);
$NC^P_{ACE}$ = number of carbon atoms present in the form of acetic acid in the product stream S(2);
$NC^P_{FA}$ = number of carbon atoms present in the form of formaldehyde in the product stream S(2).

(2) The carbon-based acrylic acid selectivity (Sel) based on the total carbon measured at the outlet is calculated as follows:

$$Sel = 100 * (NC^P_{ACR}/(NC^P_{total} - NC^P_{ACE} - NC^P_{FA}))$$

with
$NC^P_{ACR}$ = number of carbon atoms present in the product stream S(2) in the form of acrylic acid.

Figure 2:
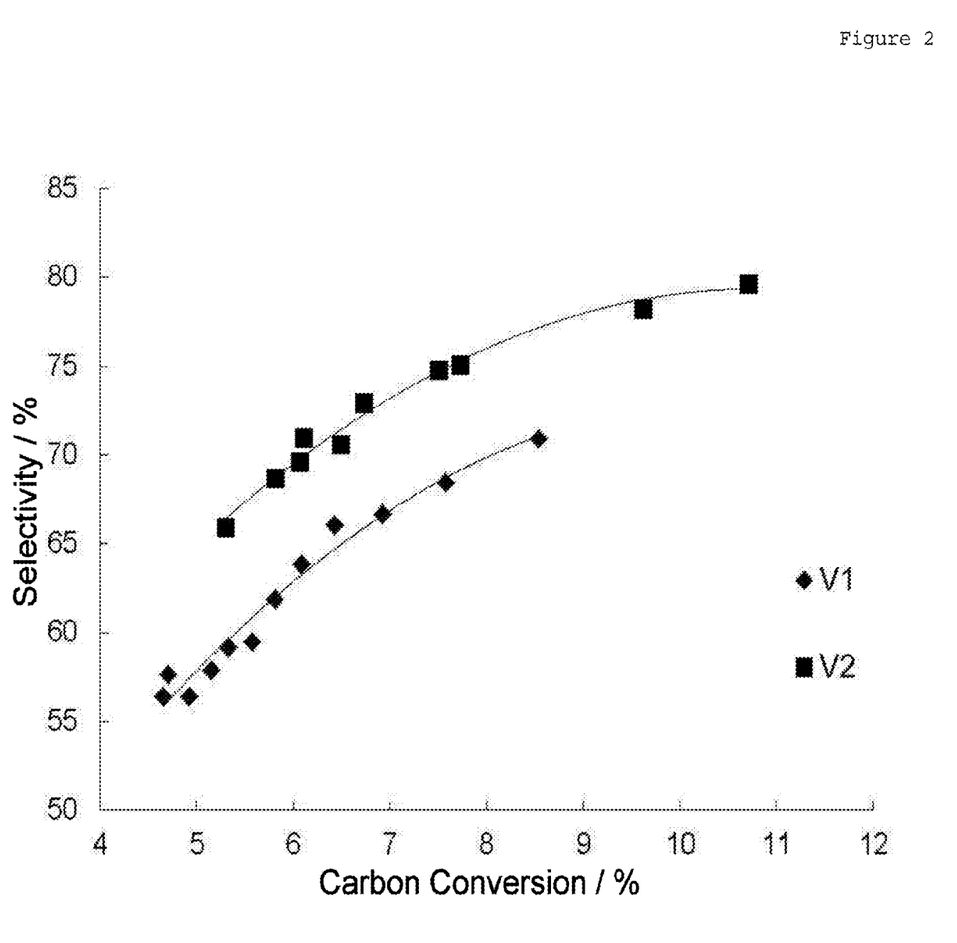
FIG. 2 shows a plot of the selectivity of acrylic acid formation (ordinate, from 50% to 85%) against the carbon conversion (abscissa, from 4% to 12%), based in each case on the total carbon measured at the outlet, for experiments V1 and V2.

As can be inferred from FIG. 2, the process of the invention (V2) shows much higher selectivities of acrylic acid formation based on the total carbon measured at the outlet than the conventional process (V1).

LITERATURE CITED

Vitcha and Sims, I & EC Product Research and Development, Vol. 5, No. 1, March 1966, pages 50 to 53

The invention claimed is:

1. A process for preparing acrylic acid from formaldehyde and acetic acid, comprising
    (a) providing a stream S(0) comprising formaldehyde and acetic acid;
    (b) reacting formaldehyde present in S(0) with acetic acid present in S(0) by means of an aldol condensation in a reaction unit comprising n reaction zones R(x) arranged in series, each comprising an aldol condensation catalyst, where n is at least 2, to obtain a stream S(n) comprising acrylic acid from the last reaction zone R(n) of the reaction unit comprising the n reaction zones arranged in series, wherein the process comprises, for each reaction zone R(x) of the reaction unit comprising the n reaction zones arranged in series:
        (i) feeding a stream S(x−1) into the reaction zone R(x);
        (ii) contacting the stream S(x−1) with the aldol condensation catalyst present in the reaction zone R(x) to obtain a stream S(x) comprising acrylic acid;
        (iii) removing the stream S(x) from the reaction zone R(x);
    wherein,
    x is an integer;
    n is at least 2;
    when x is less than n, the stream S(x) additionally comprises acetic acid and, downstream of at least one of the reaction zones R(x), the stream leaving this reaction zone R(x) as stream S(x), before being fed into the reaction zone R(x+1) immediately downstream, is mixed with a stream Z(x) comprising formaldehyde and optionally comprising acetic acid.

2. The process according to claim 1, wherein n is a number in the range from 2 to 10.

3. The process according to claim 1, wherein the molar ratio of the total amount of acetic acid fed in via streams S(0) and optionally Z(x) to the total amount of formaldehyde fed in via streams S(0) and Z(x) is equal to or greater than 1:1.

4. The process according to claim 1, wherein the molar ratio of acetic acid to formaldehyde in the stream S(0) is in the range from 2:1 to 15:1.

5. The process according to claim 1, wherein stream S(0), as well as formaldehyde and acetic acid, comprises at least one further component.

6. The process according to claim 1, wherein at least one stream Z(x), in addition to formaldehyde and optionally acetic acid, comprises at least one further component selected from the group consisting of water, oxygen, nitrogen and a mixture thereof.

7. The process according to claim 6, wherein at least one stream Z(x) comprise(s) from 0.1% to 20% by volume of oxygen.

8. The process according to claim 6, wherein at least one stream Z(x), consist(s) of water and formaldehyde to an extent of 80% by volume or more 1.

9. The process according to claim 1, wherein one stream Z(x) in each case is fed in between all the successive reaction zones R(x) and R(x+1).

10. The process according to claim 1, wherein the aldol condensation catalyst in at least one reaction zone R(x), comprises vanadium and optionally phosphorus and optionally oxygen.

11. The process according to claim 1, wherein the providing in (a) comprises:
（a-1) providing a stream comprising formaldehyde and water;
(a-2) dividing this stream comprising formaldehyde and water into at least one stream Z(x) for feeding to the process and a further stream comprising formaldehyde and water;
(a-3) mixing the further stream with a stream comprising acetic acid and optionally a stream comprising nitrogen to obtain stream S(0).

12. The process according to claim 1, wherein the reacting in (b) is effected in at least one reaction zone R(x) at a temperature in the range from 300 to 400° C.

13. An apparatus for preparing acrylic acid from formaldehyde and acetic acid, comprising a reaction unit comprising
(I) n reaction zones R(x) arranged in series, wherein the n reaction zones R(x) arranged in series each comprise an aldol condensation catalyst; and
(II) y feed devices for the feeding of at least one stream Z(x) comprising formaldehyde and optionally acetic acid, with one feed device in each case disposed between one reaction zone R(x) and one reaction zone R(x+1) directly downstream, and wherein y is an integer and is less than n; and
wherein,
x is an integer;
n is at least 2.

14. The process according to claim 1, which is performed in an apparatus comprising:
a reaction unit comprising
(I) n reaction zones R(x) arranged in series, wherein the n reaction zones R(x) arranged in series each comprise an aldol condensation catalyst; and
(II) y feed devices for the feeding of at least one stream Z(x) comprising formaldehyde and optionally acetic acid, with one feed device in each case disposed between one reaction zone R(x) and one reaction zone R(x+1) directly downstream, and wherein y is an integer and is less than n; and
wherein,
x is an integer;
n is at least 2.

15. The process according to claim 5, wherein the at least one further component comprised in stream S(0) is selected from the group consisting of water, nitrogen, oxygen and a mixture of at least two thereof.

16. The process according to claim 10, wherein the aldol condensation catalyst comprises vanadium, phosphorus and oxygen.

17. The process according to claim 16, wherein the aldol condensation catalyst comprises a vanadium-phosphorus oxide.

18. The process according to claim 17, wherein the vanadium-phosphorus oxide has the general empirical formula $V_2O_x(PO_4)_y$.

19. The process according to claim 18, wherein in the general empirical formula $V_2O_x(PO_4)_y$, x is in the range from 1.0 to 2.75, and y is in the range from 1.5 to 2.5.

20. The apparatus according to claim 13, wherein the aldol condensation catalyst is comprised in fixed bed form.

21. The process according to claim 1, wherein n is 2, 3, 4 or 5.

22. The process according to claim 1, wherein the molar ratio of acetic acid to formaldehyde in the stream S(0) is in the range from 2:1 to 10:1.

23. The process according to claim 1, wherein the molar ratio of acetic acid to formaldehyde in the stream S(0) is in the range from 2:1 to 5:1.

24. The process according to claim 1, wherein the aldol condensation catalyst in all the reaction zones R(x), comprises vanadium and optionally phosphorus and optionally oxygen.

* * * * *